United States Patent [19]
Horwitz et al.

[11] Patent Number: 5,994,346
[45] Date of Patent: Nov. 30, 1999

[54] USE OF EXOCHELINS IN THE PRESERVATION OF ORGANS FOR TRANSPLANT

[75] Inventors: Marcus A. Horwitz, Los Angeles, Calif.; Lawrence D. Horwitz, Englewood, Colo.

[73] Assignee: Regents of the University of California, Oakland, Calif.

[21] Appl. No.: 08/960,714

[22] Filed: Oct. 30, 1997

Related U.S. Application Data

[63] Continuation-in-part of application No. 08/383,180, Feb. 3, 1995, Pat. No. 5,721,209.
[51] Int. Cl.$^6$ .............................. A01N 1/02; A01N 43/46; A61K 31/55
[52] U.S. Cl. ................. 514/212; 514/11; 514/17; 514/18; 435/1.1; 435/1.2; 435/71.2; 435/118; 435/120; 435/863; 435/864; 435/865; 435/866; 530/317; 530/329; 530/330; 540/524; 540/526
[58] Field of Search .................... 435/71.2, 118, 435/120, 863, 864, 865, 866, 1.1, 1.2; 514/11, 17, 18, 212; 530/317, 329, 330; 540/528, 526

[56] References Cited

U.S. PATENT DOCUMENTS 5,280,038  1/1994  Kukreja et al. .................... 514/400

*Primary Examiner*—Frederick Krass
*Attorney, Agent, or Firm*—Koppel & Jacobs; Michael J. Ram

[57] ABSTRACT

Exochelins can be used to prevent damage to organs for transplant from the formation or presence of the ●OH radical. In particular, the invention is directed to the administration of exochelins to the organ prior to or coincidental with removal from a donor, storage, implantation in a recipient or in conjunction with reestablishment of flow of body fluids to the organ.

10 Claims, 7 Drawing Sheets

FIG. 1A

FERRIEXOCHELIN

FIG. 1B

DESFERRIEXOCHELIN

| $R_1$ | | $R_3$ | $M_r$ |
|---|---|---|---|
| $(CH_2)_N COOCH_3$ | $N=1-7$ | $H, CH_3$ | 716-828 |
| $(CH_2)_x CH=CH(CH_2)_y COOCH_3$ | $x+y=1-5$ | $H, CH_3$ | 742-826 |

(A) EXOCHELIN SATURATED SERINE SERIES

USE OF EXOCHELINS IN THE PRESERVATION OF ORGANS FOR TRANSPLANT

This application is a continuation in part of Ser. No. 08/383,180, filed Feb. 3, 1995, U.S. Pat. No. 5,721,209.

This invention was made in part with government support from NIH Grant Al-33790 and NIH Grant HL-48177.

The present invention relates to the chemical structure of a previously unidentified series of high affinity, iron-binding compounds, referred to by prior investigators as exochelins, which are released by mycobacteria. The invention also relates to modifications to these newly identified compounds to vary their physiological properties and applications of these newly identified and modified compounds.

In acute myocardial infarction, cardiac tissue is damaged by two sequential events, hypoxia in the ischemic phase and oxidative damage in the reperfusion phase. Myocardium damaged in the ischemic phase can be salvaged by reintroduction of blood to the ischemic area. However, reperfusion can result in injury as a result of an inflammatory response in the reperfused tissue caused by the migration of leukocytes into the tissue and the production of reactive oxygen species. One of the most reactive species is the hydroxyl species (●OH) which is generated in the presence of iron and which results in cell death. Prevention of the formation of ●OH will prevent lethal cell damage from this cause. It is known that the formation of ●OH is dependent on the presence of free iron and that iron chelators will prevent reperfusion injury. For example, the iron chelators deferoxamine, when administered prior to reperfusion, prevent injury and reduces myocardial infarct size during coronary artery occlusion and reperfusion. However, reperfusion injury occurs rapidly after the reestablishment of blood flow to the ischemic myocardium. Similar injury can result with the removal, storage and surgical placement of human body organs, such as heart, liver, kidney, pancreas, lung, skin, etc.

The formation of the ●OH radical is dependent on the presence of free iron; iron chelators can scavenge the free iron and thus render the iron unavailable to catalyze the hydroxyl radical formation. However, these prior known iron chelating materials either do not prevent ●OH production by the Fenton reaction (i.e., EDTA), or enter the cells too slowly (i.e., deferoxamine) such that sufficient quantities are not available to act rapidly enough to chelate enough iron to prevent the formation of ●OH and the subsequent cell destruction. Deferoxamine has been demonstrated to be effective if administered prior to occurrence of the myocardial infarct but to be ineffective if administered at or after the onset of reperfusion.

Similar injury to heart tissue can occur as a result of heart bypass procedures, such as during open heart surgery, or to other body organs when they are deprived of oxygenated blood as a result of surgery or injury.

Exochelins were briefly described and their general function in the growth of mycobacteria was discussed by Macham, Ratledge and Barclay at the University of Hull in England (Lionel P. Macham, Colin Ratledge and Jennifer C. Nocton, "Extracellular Iron Acquisition by Mycobacteria: Role of the Exochelins and Evidence Against the Participation of Mycobactin", *Infection and Immunity*, Vol. 12, No. 6, p. 1242–1251, December 1975; Raymond Barclay and Colin Ratlege, "Mycobactins and Exochelins of *Mycobacterium tuberculosis, M. bovis, M. africanum* and Other Related Species", *Journal of General Microbiology*, 134, 771–776, (1988); L. P. Macham and C. Ratledge, "A New Group of Water-soluble Iron-binding Compounds from Mycobacteria: The Exochelins", *Journal of General Microbiology*, 89, 379–282, (1975)). Macham identified the existence of a substance found in the extracellular fluid, which he referred to as exochelin. He described exochelin as a water and chloroform soluble compound which has the ability to chelate free iron. According to Macham, this material has similarities to mycobactin, which is located in the cell wall and functions to transmit iron to the interior of the cell. However, in contrast thereto, mycobactin is a lipophilic, water insoluble molecule which is unable to diffuse into, and assimilate free iron from, the extracellular environment. Macham recognized that exochelin functions at physiological pH to sequester iron from other iron bearing compounds in the serum, such as transferrin or ferritin, and present the iron in a form that can be transferred to mycobactin. Macham et al. did not isolate or purify the exochelins but identified them as a penta- or hexapeptide, having a molecular weight of 750 to 800, containing 3 mol of ε-N-hydroxylysine, εN-acetyl-εN-hydroxylysine, or εN-hydroxyornithine and 1 mol of threonine. Also, depending on the bacterial source of the exochelin, he disclosed that the molecules may also include β-alanine or salicylic acid. We have since proven that Macham et al. did not have the correct structure for the exochelins.

Barclay (ibid) described the production of a material referred to as exochelins from twenty-two different strains of *M. tuberculosis* and related species. However, these prior investigators did not determine the specific structure of exochelins or identify any applications of the exochelins other than their function as a transport medium for iron to mycobactin located in the cell wall.

Thus there is a need for a substance that can be easily administered at the time of reperfusion and which will rapidly chelate the free iron as it is formed or made available to prevent the formation of the ●OH radical. Further, there is a need for a composition which will improve the ability to store organs for transplant and increase the viability of those organs once implanted. Still further, there is a need to identify the specific structure of exochelin so that its function can be more fully understood and its utility as a diagnostic, treatment and preventive modality can be elucidated.

SUMMARY

These needs are met by the present invention which comprises the use of exochelins to prevent damage to living tissue in organs for transplant, presumably from the formation or presence of the ●OH radical. In particular, the invention is directed to the administration of exochelins to the organs prior to removal, during storage and transportation, or prior to or coincidental with or shortly after reestablishment of flow to the organ to prevent damage to the implanted organ from iron mediated free radical formation. Also presented is the chemical structure of exochelins and modified exochelins.

DRAWINGS

These and other features, aspects and advantages of the present invention will become better understood with reference to the following description, appended claims, and accompanying drawings, where:

DETAILED DESCRIPTION

It has been found that exochelins can block, or significantly reduce damage to living tissue, particularly, oxidative damage to tissue resulting from the iron-mediated catalysis of tissue/free radicals reactions, such as the hydroxyl radical ●OH, particularly hydroxyl radicals generated in the Fenton reaction, as occurs upon reintroduction of blood flow to ischemic tissue and is commonly referred to as reperfusion injury. It has been further found that the exochelins are effective to retard or prevent reperfusion injury when administered at the start of or concurrent with reperfusion. Additionally, it has been found that exochelins encompass a much broader class of materials and have a different chemical structure then originally theorized by Macham et al. and Barclay et al.

It has also been found that these materials can chelate a broad range of metals to result in materials not previously known. Besides preventing reperfusion injury, properly modified exochelins can be used to treat certain diseases, attack certain cells, such as cancer cells, and be used to monitor the effectiveness of drug treatment and detect the presence of certain disease states. In particular, it is known that the growth of neuroblastoma cells can be negatively affected by the removal of iron using the iron chelating compound desferrioxamine without similarly affecting the growth of normal cells. Other applications of exochelins include treatment of iron overload from transfusions or cancer chemotherapy, particularly for leukemia.

As a result of isolating and purifying exochelins, it has been found that exochelins are a family of molecules having a range of molecular weights and various different side chains. Further, purified exochelins have been prepared and their utility as scavengers of free iron, such that they are effective in preventing the formation of tissue damaging hydroxyl radicals ●OH, has been demonstrated for the first time. In particular, purified exochelins of *M. tuberculosis* have been isolated and have been shown to effectively remove iron from transferrin, lactoferrin and ferritin at physiological pH without transmitting any of the infectious properties of the bacteria from which they are derived. It has also been demonstrated for the first time that these exochelins block hydroxyl radical formation by the Fenton reaction and, based on the response of cardiac myocytes, can be effective to prevent reperfusion injury after myocardial infarction or vascular insults to other tissue when administered after the attack occurs as well as for several hours after the episode.

Figure 1A:
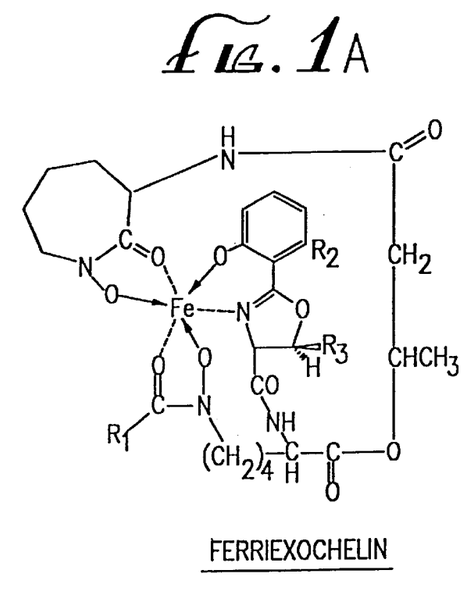
FIGS. 1*a, b* and *c* show the chemical structure of an iron chelate of exochelin (ferriexochelin) and the desferriexochelin (iron free) molecule.
Figure 1B:
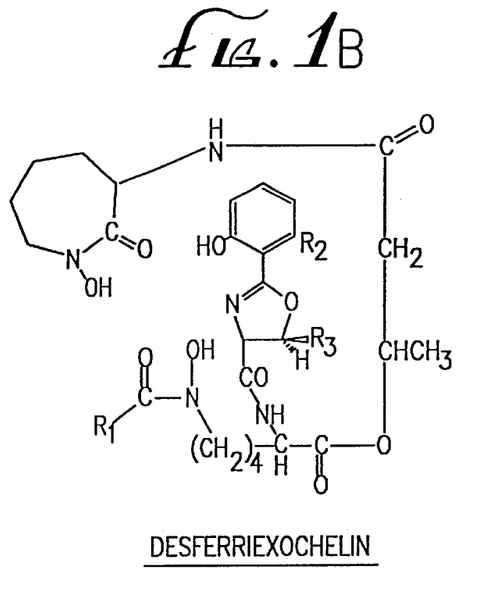
Figure 1C:
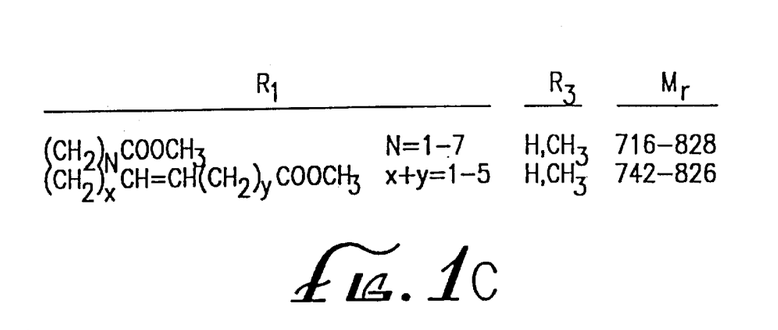

While mycobactins have been extensively studied, individual exochelins had not been isolated or purified and their structure and composition had not been previously defined. Further, we have found that prior references have mischaracterized the exochelins, and thus have failed to identify the structure of these compounds. In particular, Macham (ibid.) identified them as a penta- or hexapeptide, having a molecular weight of 750 to 800, containing 3 mol of $\epsilon$-N-hydroxylysine, $\epsilon$N-acetyl-$\epsilon$N-hydroxylysine, or $\epsilon$N-hydroxyornithine and 1 mol of threonine. We have found that the exochelins have a much broader range of molecular weights, constitute several series of compounds with an identifiable difference in molecular weights, include only 2 mol of $\epsilon$-N-hydroxylysine and are not peptides. A peptide is a polymer of an amino acid ($NH_2$—CHR—COOH) formed by the condensation of the carboxylic group of a first molecule with the amino group of another molecule to form an amide linkage (—CO—NH—). Exochelins cannot be considered to be peptides. Instead, they contain three amino acids and other structural moieties (salicylic acid, dicarboxylic acids or monoester analogs, and hydroxy carboxylic acids) formed by amide (—NH—CO—), hydroxymate (—NH(OH)—CO—) and ester condensations (—CO—O—). The ferri- and desferri forms are shown in FIG. 1.

Preparation—Exochelins were generated and purified from a virulent (Erdman) and avirulent (H37Ra) strain of *M. tuberculosis*. To enhance the production of *M. tuberculosis* exochelins the bacteria were cultured in an iron deficient medium. In particular, the Erdman strain of *M. tuberculosis* (American type culture collection 35801) and H37Ra strain (ATCC 25177) were grown on Middlebrook 7H11 agar plates at 37° C. in 5% $CO_2$. After 14 days the bacteria were harvested, suspended in 150 ml of modified Sauton's medium in culture flasks and incubated for 3 to 8 weeks. The modified Sauton's medium contained 0.12 mg/l ferric ammonium citrate without added surfactant.

Iron rich exochelins (ferriexochelins) were then recovered by filtering, saturating with iron and extracting with chloroform and purified by high pressure liquid chromatography (HPLC). Specifically, the supernatant fluid from the above suspension was filtered through successive 0.8 $\mu$m and 0.2 $\mu$m low-protein binding filters. The exochelins were then loaded with iron by saturating the filtered supernatant fluid by exposure to ferric chloride (150 mg per liter of culture filtrate). The ferric-exochelins were mixed with chloroform (1 volume of culture filtrate per 1.5 volumes of chloroform) and, after separation of the layers, the exochelin rich chloroform layer was removed and stored under anhydrous magnesium sulfate (2 g/l). The chloroform extract was then passed through a fritted glass filter and evaporated by rotary evaporation leaving behind a brown residue.

Figure 2A:
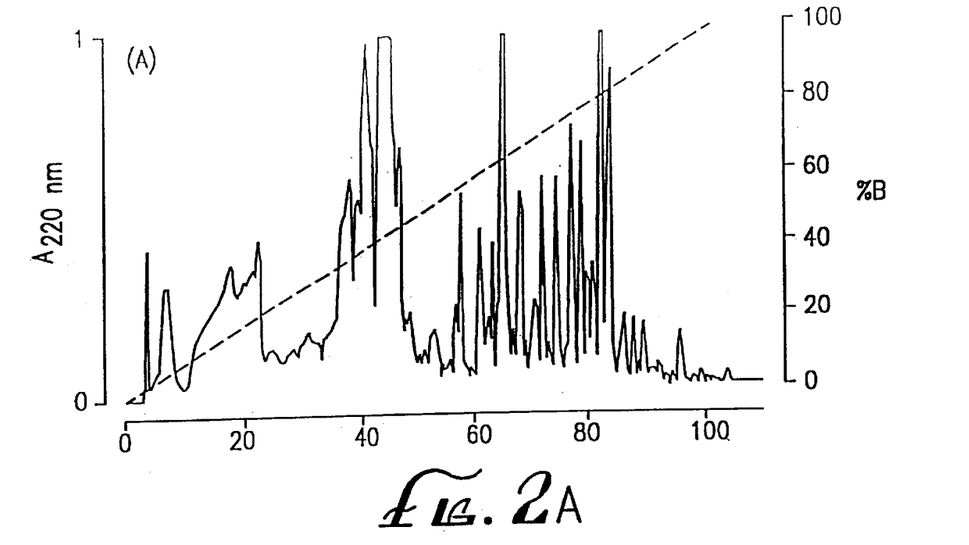
FIGS. 2*a* and *b* show an elution profile of a culture filtrate of *M. tuberculosis* monitored at 220 nm and 450 nm.
Figure 2B:
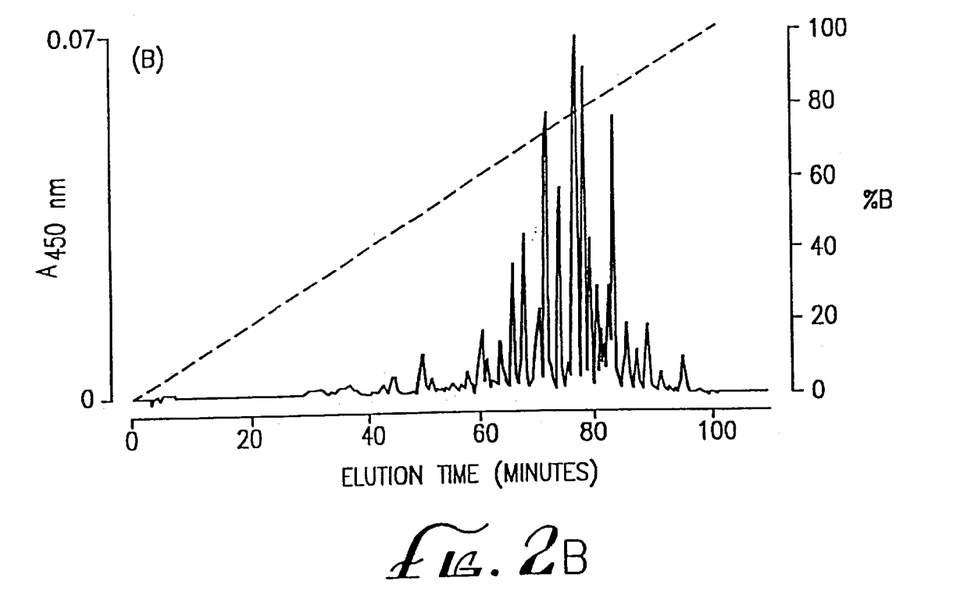
Figure 3:
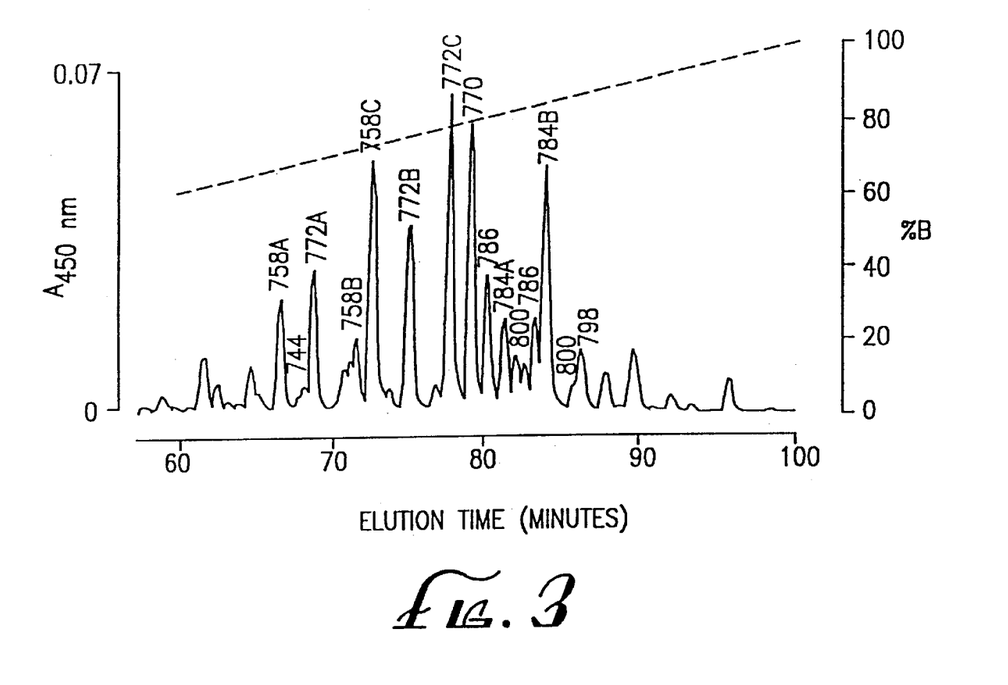
FIG. 3 shows an elution profile of the same filtrate monitored at 450 nm with the molecular weight of each peak shown.
Figure 4A:
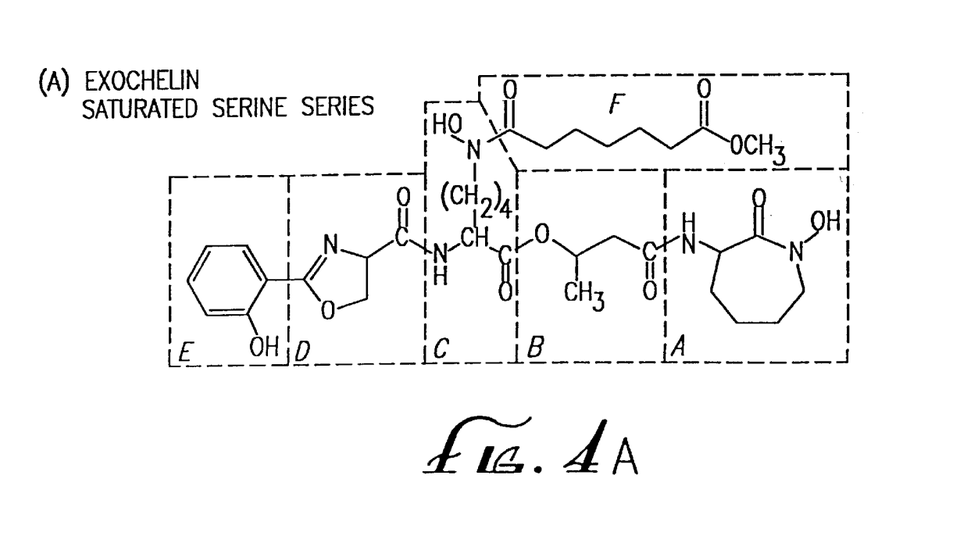
FIGS. 4a and b show the mass spectrometer spectra of a major serine-containing exochelin at m/z=720.3 along with the structure determined therefrom.
Figure 4B:
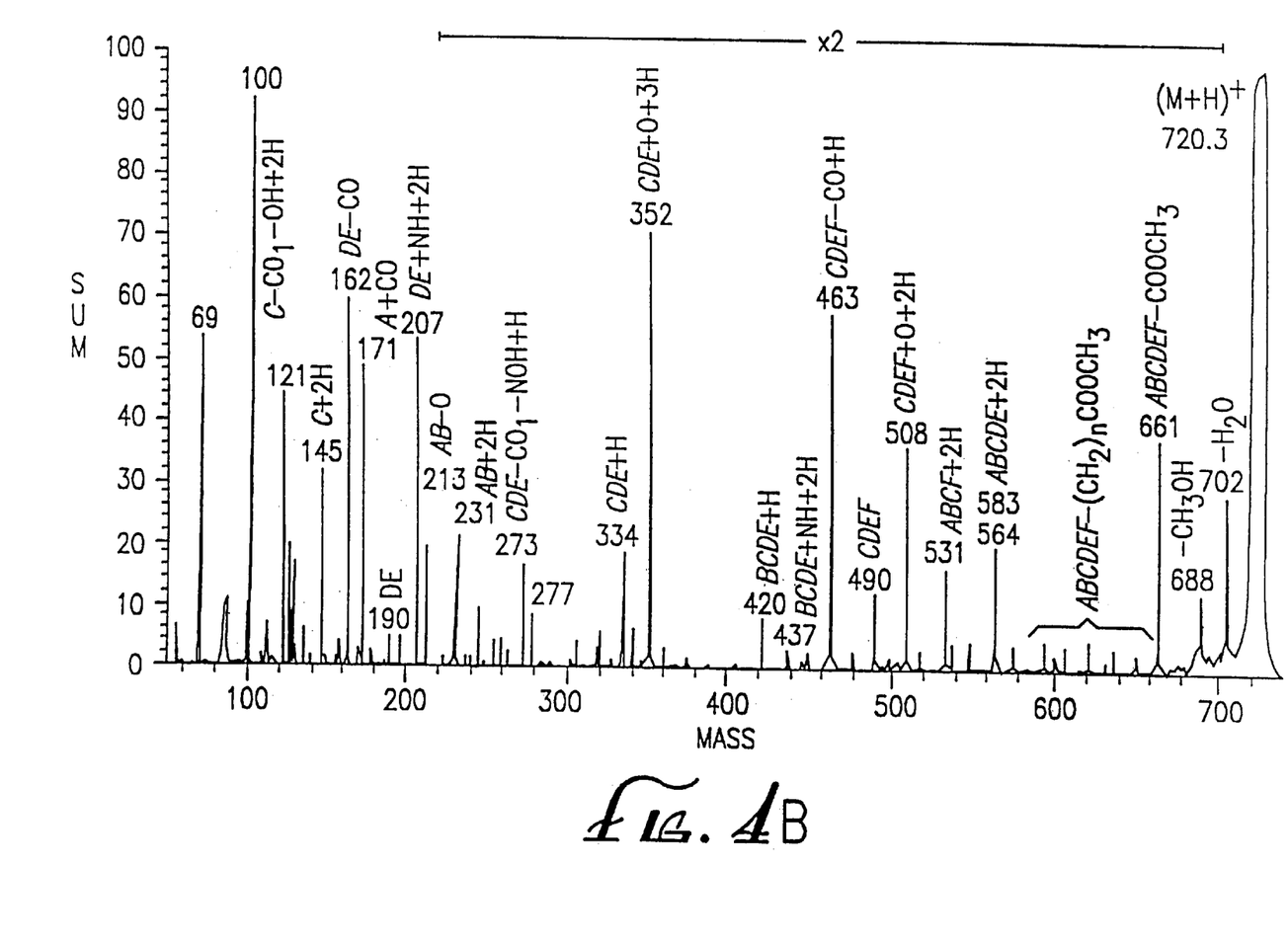
Figure 5:
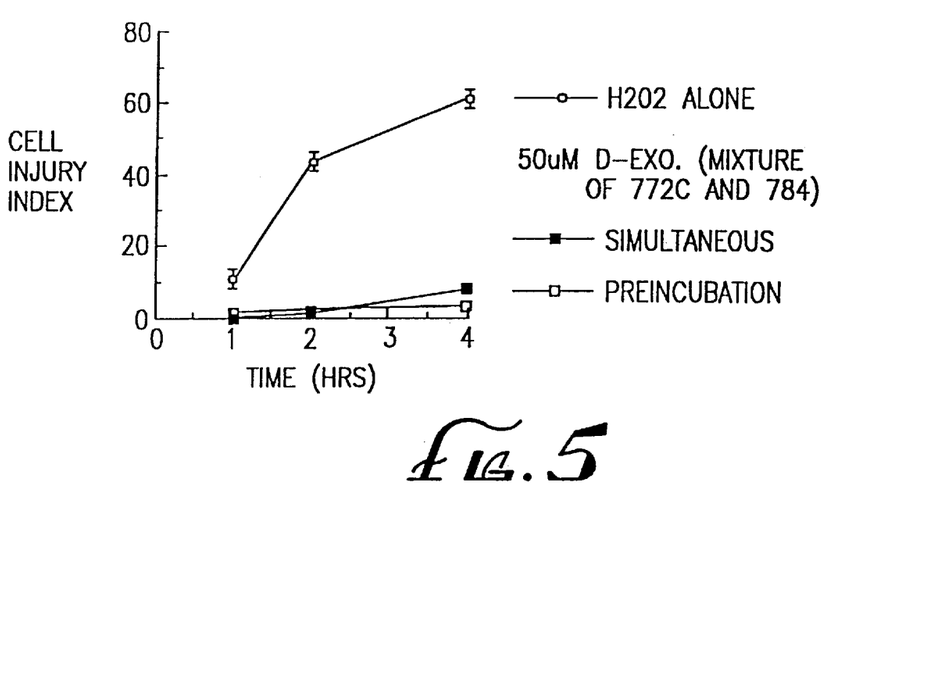
FIG. 5 is a graph showing the inhibition of cell injury as a result of the use of an exochelin mixture on cardiac myocytes.
Figure 6:
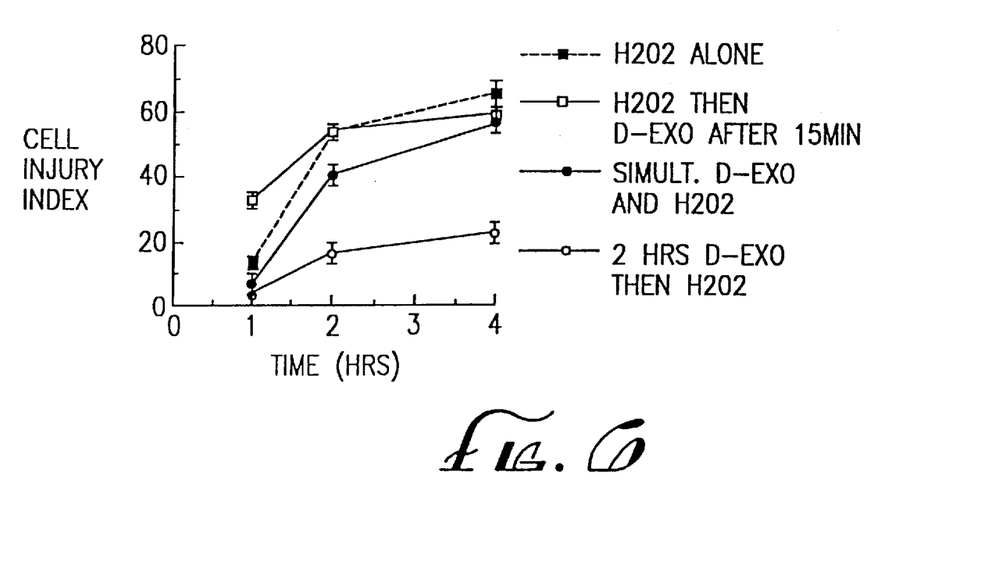
FIG. 6 is a graph showing the inhibition of cell injury as a result of the use of exochelin 758C on cardiac myocytes.
Figure 7:
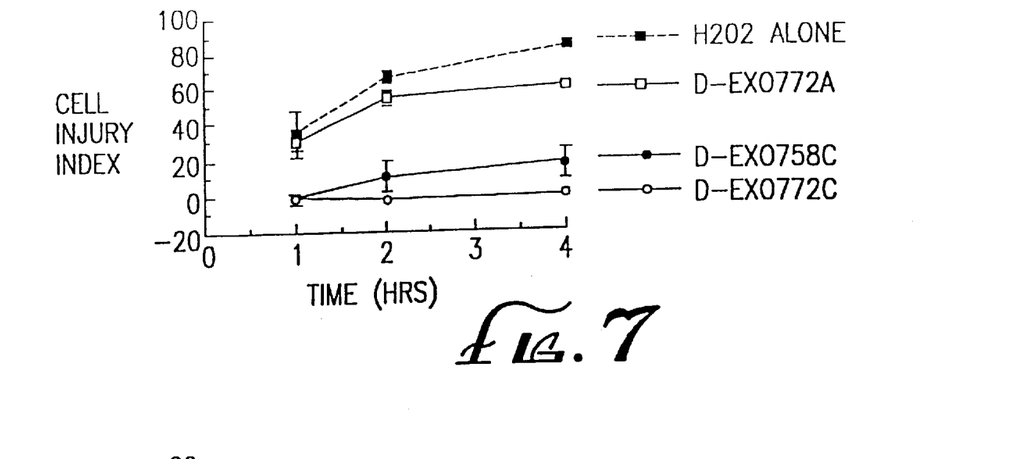
FIGS. 7, 8, and 9 are graphs comparing the inhibition of cell injury as a result of the use of exochelin 758C, 772A and 772C on cardiac myocytes.
Figure 8:
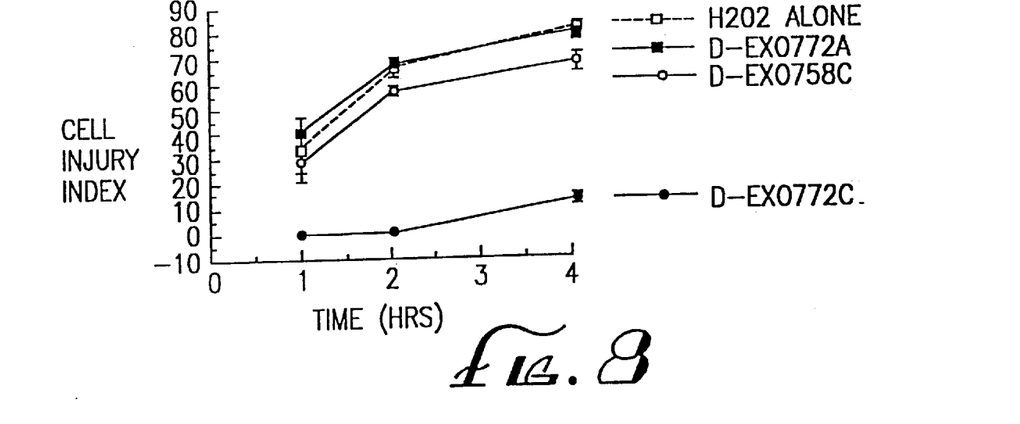
Figure 9:
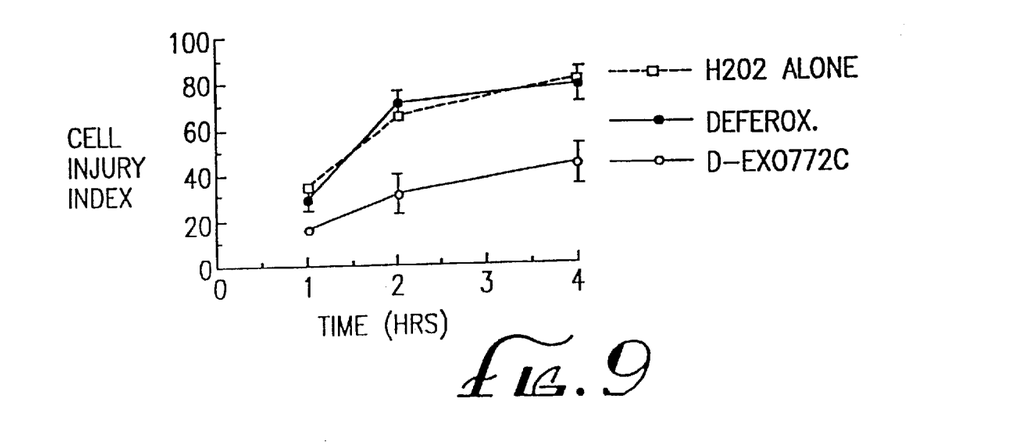

The brown residue was further purified by suspension in 5 ml of a first buffered solution (0.1% trifluoroacetic acid) which was introduced into a liquid chromatography column (C-18 Sep-Pak cartridge). The brown band which formed near the top of the column was eluted with a second buffer (0.1% TFA, 50% acetonitrile). The partially purified material was then diluted three-fold in 0.1% trifluoroacetic acid and subjected to reverse phase high pressure liquid chromatography at a rate of 1 ml/min followed by exposure to a C-18 column. The presence of the iron rich exochelins in the HPLC eluate was detected by simultaneous monitoring of the UV absorbance of the 450 nm peak (iron compounds) and the 220 nm peak which is indicative of amide and aromatic groups. Approximately 5 major and 10 minor peaks, shown in FIG. 2, eluted out of the final C-18 column exhibited a high 450/220 nm absorbance ratio. These were confirmed to be exochelins by mass spectrometry. Major peaks were further purified by a second reverse phase HPLC on an alkyl-phenyl column. The exochelins recovered from the Erdman strain of *M. tuberculosis* were identical to the exochelins recovered from the H37Ra strain.

Characterization—Based on LSIMS and ESI-MS analysis of the numerous peaks, in their ferr- ($Fe^{3+}$) form, eluted from the column (see FIG. 3), the iron-exochelins are not confined to the two specific molecules detailed above but include a family of species ranging in mass from 716 to 828 daltons. Each member of the family appears to differ from its neighbor by 14 daltons, reflecting the number of $CH_2$ groups in the $R_1$ alkyl side chain and/or 2 daltons, reflecting the presence of a double bond in the $R_1$ alkyl side chain. Accordingly, the exochelins appear to form two series with the subsequent members of each series differing in mass by 14 daltons, the saturated series having masses of approximately 716, 730, 744, 758, 772, 786, 800, 814 and 828 daltons and the unsaturated series having masses of 742, 756, 770, 784, 798, 812 and 826. Additionally, the presence or absence of a methyl group at $R_3$ (i.e., H or $CH_3$) further defines an additional two series of molecules referred to as the serine ($R_3$=H) and the threonine series ($R_3$=$CH_3$), as confirmed by amino acid analysis. The most polar compounds are to the left of the figure (elute earlier) and the least polar (most soluble in lipid) are to the right. However all the peaks are water soluble. Where more than one peak was found to have the same molecular weight each peak is further designated A, B or C (i.e., 758A, B and C) to indicate the level of polarity with A representing the more polar compound and the C representing the less polar form. The more polar forms are believed to result from methyl groups attached at different locations in the molecule, shorter $R_1$ side chains, and/or the conversion of the methyl ester at the terminus of $R_1$ to a carboxylic acid moiety.

Structure of the Exochelin—FIG. 4 shows the results of tandem mass spectrometric analysis under induced dissociation (He floated at 2 keV for a collision energy of 6 keV) of the major saturated serine-containing desferriexochelin with $(M+H)^+$ at m/z 720.3. The fragment ions were assigned to one of the six structural moieties A–F resulting from the cleavage products generated about the amide or ester bonds with the hydrogen transfer relative to the neutral molecule associated with each peak indicated on the spectrum shown in FIG. 4. Acid hydrolysis and methylation of the exochelins resulted in the formation of salicylic acid and pimelic acid. The mass spectrographic analysis indicates that the pimelic acid is present in the exochelin as a methyl ester.

Based on this analysis the general structure of the ferriexochelins and the desferriexochelins is shown in FIG. 1. The methyl group shown at the $R_4$ position (as defined in FIG. 10) may be in the $R_6$ position. The iron-exochelin core molecule is circular with iron in the center. It contains 3 amino acid moieties (two N-hydroxylysines and 1 serine or threonine, depending on whether $R_3$ is a hydrogen or methyl group). The major difference between exochelins and mycobactins of *M. tuberculosis* is that $R_1$ in the exochelins exists as either a saturated alkyl methyl ester ($(CH_2)_NCOOCH_3$) or a singly unsaturated alkyl methyl ester $(CH_2)_xCH=CH(CH_2)_yCOOCH_3$ and exochelins have a much shorter alkyl side chain than mycobactins with these shorter side chains terminating in methyl ester moieties. These differences provide for the water solubility of the exochelins and their ability to function in the extracellular environment.

Clinical Utility—The clinical utility of the administration of exochelins to prevent reperfusion injury or protect transplanted organs was demonstrated by application to adult rat myocytes.

In the Examples below the different exochelins, in both the desferri- and ferr- form, will be identified by the molecular weight as shown in the elution curve in FIG. 3.

EXAMPLE 1

The heart of a male rat was excised after the rat was anesthetized, a thoracotomy performed and the heart chilled in situ. The excised heart was then placed on a Langendorff apparatus and perfused with a collagenase and hyaluronidase in a 50 $\mu$M calcium in modified Krebs Ringer buffer solution. The tissue was then finely divided and dispersed in a collagenase/trypsin solution, filtered into a cold trypsin inhibitor solution and exposed to increasing concentrations of calcium. After removal of damaged cells, the remaining cell suspension was placed in several laminin-coated plastic dishes along with a culture medium containing 5% fetal bovine serum.

After the cultures were allowed to sit for 48 hours hydrogen peroxide was added to each dish and the lactate dehydrogenase activity (LDH), which is indicative of cell injury, was measured at various time intervals. A cell injury index (CII) for comparison purposes was obtained by measuring the LDH in a nonexposed cell culture in both an as is condition (0 Index) and following exposure to a detergent that lysis 100% of the myocytes (1% Triton X-100) representing a CII of 100. The LDH under specified treatment conditions for various periods of time was then determined, the corresponding CII value determined and the individual results were plotted against time (FIG. 5).

Using the procedure described above, a mixture of the desferri- form of exochelins 772C and 784 (a 50:50 mixture of the 772C peak and the 784 peak), a relatively non-polar substance, was isolated and used to treat cell cultures. The exochelins were converted to the desferriexochelin form by incubation for several hours with 50 millimolar EDTA at pH 6. The desferri-form was then repurified by chloroform extraction.

Three samples of cells were exposed to either a) $H_2O_2$, b) $H_2O_2$ and 50 $\mu$M of desferriexochelin (iron free exochelin) added simultaneously or c) $H_2O_2$ added 2 hours after addition of 100 $\mu$M of desferriexochelin to the cell culture (preincubation). The untreated cell cultures showed almost 62% cell injury over a 4 hour period. In contrast thereto, addition of exochelin simultaneously with, or 2 hours prior to, peroxide addition substantially prevented or significantly reduced cell damage, the cell injury being approximately 2 to 9%.

EXAMPLE 2

The procedure of Example 1 was repeated with desferriexochelin 758C which is relatively more polar than exochelins 772C and 784. There was little or no difference between the effect when desferriexochelin 758C was delivered along with or within 15 minutes of delivery of $H_2O_2$. In both instances after 2 hours the cell destruction was substantially the same as in the control. However, delivery of the desferriexochelin 758C 2 hours prior to $H_2O_2$ introduction cut the cell destruction to a CII of about 20. The results are shown in FIG. 6.

EXAMPLE 3

The procedure set forth above was repeated using desferriexochelin 772A, 772C and 758C. Plotted in FIGS. 7–9 are the results for 2 hour predelivery, simultaneous delivery and 20 minute delayed delivery of the exochelins. Only exochelin 772C shows marked retardation of injury under all conditions while exochelin 772A is not highly effective under any conditions. On the other hand, exochelin 758C shows strong protection only if delivered 2 hours prior to peroxide introduction. It is therefore concluded that the relatively non-polar, more lipid soluble exochelins are effective when administered with or after formation of the ●OH radical, i.e., after injury occurs; the more polar exochelins must be administered 1 to 2 hours prior to the free radical generating event to prevent or reduce cell destruction.

EXAMPLE 4

The capacity of exochelins to compete for iron with host iron-binding proteins was determined by incubating desferriexochelin with solutions of transferrin, lactoferrin, or ferritin at 4:1 and 1:1 molar ratios of iron to exochelin. The conversion of the exochelin from its desferri- to its ferr-form was then determined by reverse phase HPLC. Within one minute of exposure of desferriexochelin to 95% iron-saturated transferrin, the exochelin had started to pick up iron from the transferrin and within one hour the exochelin was fully saturated with iron. Iron was also readily removed from 40% iron-saturated transferrin, which approximates the iron level in transferrin as it exists in serum. Similar results were obtained when desferriexochelin was exposed to iron-saturated lactoferrin. Likewise, ferritin released iron to the exochelin but at a slower rate than other iron binding proteins.

It has been discovered that exochelins are very effective in scavenging free iron in a physiological system and withdrawing iron from iron bearing protein. In particular it has been found that exochelins effectively block the formation of the hydroxyl free radical ●OH and thus significantly reduce or prevent the injury to ischemic tissue when circulation of blood to that tissue is reestablished with the higher molecular weight, less polar exochelins being more effective in preventing cell destruction. While the benefit to cardiac tissue has been demonstrated, the benefit of the use of exochelins following interruption of blood flow to other body organs, including but not limited to the brain, kidney, liver, bowel, and skeletal muscle is now apparent.

In light of Example 1, it also is apparent that desferri-Exochelins will be of use for preserving transplanted organs, which suffer an interruption of blood flow from the time they are removed from the donor until they are transplanted into the recipient. The desferri-Exochelins can be added to any of the various preservation solutions presently used for that purpose such as the University of Wisconsin solution (ViaSpan); Roe's Solution; Collins-2 Solution; Histidine-tryptophan-ketoglutarate Solution; St. Thomas Hospital's Cardioplegic Solution II; Bretschneiders' Solution; cold saline solution; or a cold blood cardioplegia solution. It is believed that the utility of any solution suitable for preserving organs can be improved by addition of exochelins to the solution, the addition resulting in an increased viability of the organ after transplant and an improved capability to store viable organs and tissue. While the benefit to cardiac tissue has been demonstrated, the benefit and use of desferri-Exochelins for preservation of other body organs, including but not limited to the kidney, liver, pancreas, and lung is now apparent. Likewise, it is believed that use of exochelins may improve the viability of skin, particularly in the treatment of severely burned patients.

While it is believed that the benefits of administration of the exochelins are increased by the earliest use of exochelin in the transplant process, use in any stage of the process, i.e. prior to removal from the donor body, during storage, immediately prior to placement in the recipient's body, in conjunction with reinstituting fluid flow to the organ in the recipient or up to 60 minutes after reestablishment of fluid flow, will increase the viability of the transplanted organ and the healthful outcome of the recipient thereafter.

Experimentation has shown that the affinity of the exochelins is not limited to iron but that other metals can be chelated, such as Na, K, Mn, Mg, Al and Zn. Therefore, the exochelins can be used to deliver to the body various desirable metals or chelate various undesirable metals within the body. Additionally, certain cells, including certain cancer cells are known to have a need for or affinity for certain metals. This can be utilized to deliver to that cell reactive compounds attached to the exochelins for destruction of the cell (chemotherapy) or to target a diseased organ with a beneficial drug bound to the exochelin. Conversely, since certain cancer cells have a high demand for iron, the desferriexochelins can be used to bind free iron, thus preventing iron delivery to the cancer cell, resulting in the destruction of the cancer cell.

While the structure of exochelins recovered from *M. tuberculosis* is shown in FIG. 1, it is known that other mycobacteria can generate exochelins and that these exochelins may have different structure and include different amino acids depending on the mycobacteria from which they are derived. However, all exochelins will behave in a similar manner and exist in similar series with subsequent members thereof having a similar progression of molecular weights. The effectiveness of the different members of the series will also depend on the relative polarity of the molecules. Therefore, the invention contemplates exochelins generated from other mycobacteria including, but not limited to, *M. tuberculosis , M. microti, M. bovis, M. africanum, M. kansasii, M. marinum, M. gastri, M. nonchromogenicum, M. terrae, M. trivale, M. malmoense, M. shimoidei, M. gordonae, M. asiaticum, M. szulgai, M. simiae, M. scrofulaceum, M. avium, M. intracellulare, M. xenopi, M. ulcerans, M. haemophilum, M. farcinogenes, M. lepraemurium, M. paratuberculosis, M. chelonae* subsp. *chelonae, M. chelonae* subsp. *abscessus, M. fortuitum, M. chitae, M. senegalense, M. agri, M. smegmatis, M. phlei, M. thermoresistibile, M. aichiense, M. aurum, M. chubuense, M. duvalii, M. flavescens, M. gadium, M. givum, M. komossense, M. neoaurum, M. obuense, M. parafortuitum, M. rhodesiae, M. sphagni, M. tokaiense* or *M. vaccae*.

Figure 10A:
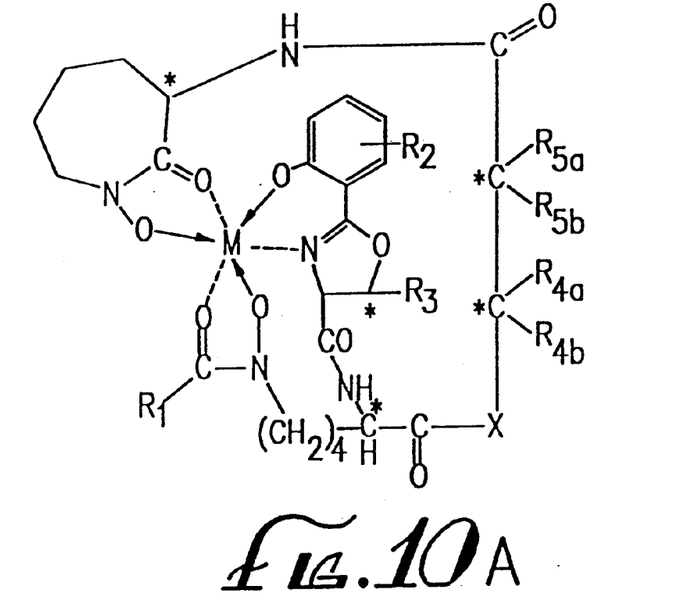
FIGS. 10a and b shows the chemical structure of an iron chelate of exochelin (ferriexochelin) and the desferriexochelin (iron free) molecule with sites for modification identified.
Figure 10B:
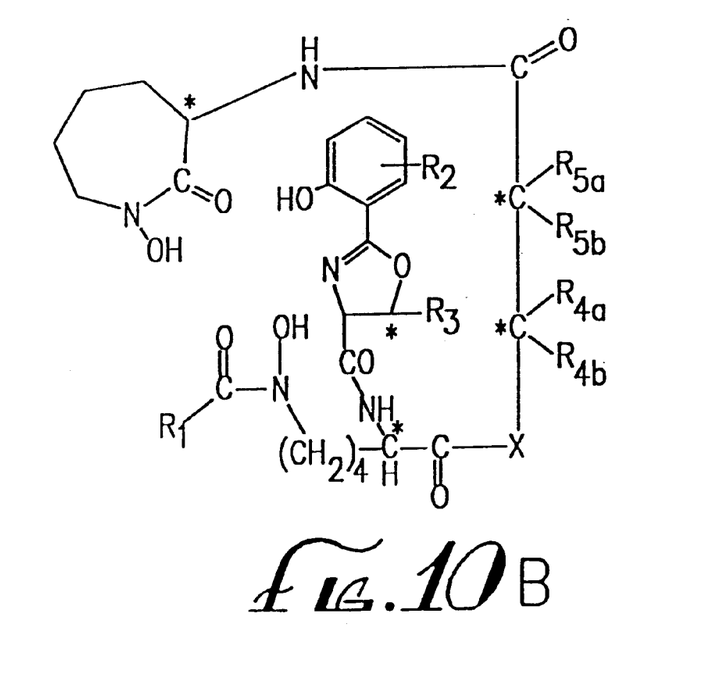

It is also contemplated that exochelins can be modified to affect their solubility properties, metal chelating ability or cellular absorption rates. Additionally, detection of modified exochelins or exochelin in their metal chelated state, using monoclonal antibodies or chemical analysis as diagnostic tools, by blood analysis, urinalysis or noninvasive instrumental techniques, to monitor progress of a disease state or effectiveness of treatment. In particular, referring to the structures of the metal containing and metal free compounds shown in FIG. 10, the following substitutions are contemplated:

$R_1 = (CH_2)_n CH_3$ as a linear or branched chain; $(CH_2)_n COOH$, a fatty acid; $(CH_2)_n COOR$, a fatty acid ester where R is an alkyl group; $(CH_2)_n CONH_2$;

$R_2$ = a substitution at any of the 4 open ring sites of alkyl groups, sulfonamides, hydroxyl, halogen, acetyl, carbamyl, amines, $NO_2$ or any combination thereof;

$R_3$—the H (serine) or $CH_3$ (threonine) can be replaced by side chains found on β-hydroxy amino acids which are capable of forming cyclic oxazoline structures.

$R_{4a}$ and $R_{4b}$=H, $CH_3$ or other alkyl or substituted alkyl groups;

$R_{5a}$ and $R_{5b}$=H, $CH_3$ or other alkyl or substituted alkyl groups;

X=O, NH, S, $CH_2$;

M=mono-, di-, or trivalent metals such as Pb, Al, Cd, Ni, Ag, Au, As, Mg, Mn, Zn, Cu, Ru, Nb, Zr, Ta, V, Ga, Pt, Cr, Sc, Y, Co, Ti, Na, K;

* represents chiral centers which may be R or S;

The various hydroxyl groups (—OH) involved in chelating the metal can be replaced by various functional groups, such as H or a halogen, to vary the affinity of the compound for the chelated metal or to convert the molecule into a metal antagonist.

Although the present invention has been described in considerable detail with reference to certain preferred versions and uses thereof, other versions and uses are possible. For example, exochelins can be used to attack infectious bacteria, such as *M. tuberculosis*, by blocking access of the mycobacteria to iron, to remove toxic levels of metals from the body or to deliver desirable metals to the body. Further, modified metal containing exochelins can deliver appended active drugs or chemicals to sites in the body which preferentially absorb the chelated metal and preferentially absorbed exochelins with chelated metals can be used as targets for treatment by other modalities, such as microwave energy for hypothermia treatment of cancer cells. Therefore, the spirit and scope of the appended claims should not be limited to the description of the preferred versions contained herein.

What is claimed is:

1. A method of protecting mammalian organs for transplant from injury resulting from exposure to hydroxyl free radicals formed following reestablishment of flow of body fluids to that organ after implantation in a recipient's body comprising administering a composition which contains an effective amount of at least one desferriexochelin to the organ.

2. The method of claim 1 wherein the desferriexochelin is administered to the organ before removal from the donor body.

3. The method of claim 1 wherein the desferriexochelin is administered at least as early as the time the organ is placed in the recipient body and the administration of the body fluid to the organ is reestablished.

4. The method of claim 1 wherein the desferriexochelin is administered within about sixty minutes following the start of the flow of the body fluid to the organ in the recipient body.

5. The method of claim 1 wherein the desferriexochelin is administered during storage of the organ following removal from the donor body.

6. The method of claim 1 wherein the mammalian organ is selected from the group consisting of heart, lung, kidney, liver, pancreas and skin.

7. The method of claim 1 wherein the composition contains an effective amount of at least one desferriexochelin which has the formula:

wherein $R_1$ is selected from the group consisting of $(CH_2)_N COOCH_3$ and $(CH_2)_x CH=CH(CH_2)_y COOCH_3$ with N being from 1 to 7 and x+y being from 1 to 5, $R_2$ is a chemical moiety substituted at any of four open sites on the phenyl ring, said chemical moiety being selected from the group consisting of alkyl groups, sulfonamides, hydroxyl, halogen, acetyl, carbonyl, amines, and $NO_2$ and combinations thereof, and $R_3$ is selected from the group consisting of H and $CH_3$, said desferriexochelin having a molecular weight of from about 663 to about 775 daltons.

8. The method of claim 7 wherein the composition includes a mixture of desferriexochelins having a molecular mass of 719 and 731 daltons.

9. The method of claim 7 wherein the composition includes a mixture of nonpolar desferriexochelins characterized by N being a whole number from 5 to 7.

10. The method of claim 7 wherein the composition includes a mixture of nonpolar desferriexochelins characterized by x+y being 4 or 5.

* * * * *